United States Patent [19]

Fujimori et al.

[11] 4,101,670
[45] Jul. 18, 1978

[54] GERMICIDAL AND ACARICIDAL COMPOSITIONS

[75] Inventors: Kunihiko Fujimori; Kuniaki Shimizu, both of Shimizu; Haruki Ogawa, Fujieda, all of Japan

[73] Assignee: Kumiai Chemical Industry Co., Ltd., Tokyo, Japan

[21] Appl. No.: 714,861

[22] Filed: Aug. 16, 1976

[30] Foreign Application Priority Data

Aug. 15, 1975 [JP] Japan .................... 50-99144

[51] Int. Cl.$^2$ ............... C07C 153/09; A01N 9/12
[52] U.S. Cl. ..................... 424/300; 260/455 A; 71/100
[58] Field of Search ............. 260/455 A; 71/100; 424/300

[56] References Cited

U.S. PATENT DOCUMENTS

| | | | |
|---|---|---|---|
| 3,142,693 | 7/1964 | Weiss et al. | 260/455 A |
| 3,166,401 | 1/1965 | Weiss et al. | 71/100 |
| 3,205,248 | 9/1965 | Weiss et al. | 260/455 A |
| 3,225,078 | 12/1965 | Weiss et al. | 71/100 |
| 3,265,562 | 8/1966 | Watts | 260/455 A |
| 3,277,142 | 10/1966 | Zerbe et al. | 260/455 A |
| 3,284,184 | 11/1966 | Zerbe et al. | 71/100 |

OTHER PUBLICATIONS

Wagner & Zook, "Synthetic Organic Chemistry," 1953, pp. 226–228, 232–233.

Primary Examiner—Lewis Gotts
Assistant Examiner—Robert C. Whittenbaugh
Attorney, Agent, or Firm—Sughrue, Rothwell, Mion, Zinn and Macpeak

[57] ABSTRACT

A composition useful as herbicides, germicides, and acaricides without showing toxicity to men and beasts as well as to fish and shellfishes containing as the active ingredient the compound represented by the general formula

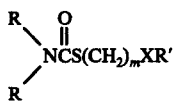

wherein R represents a lower alkyl group; R' represents a group shown by the formula

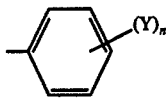

(wherein Y represents a halogen atom, an alkyl group, an alkoxy group, a nitro group, a methylthio group, or a trifluoromethyl group and n is an integer of 0 to 3); X represents an oxygen atom or a sulfur atom; and m is an integer of 3 to 6.

10 Claims, No Drawings

GERMICIDAL AND ACARICIDAL COMPOSITIONS

DETAILED DESCRIPTION OF THE INVENTION

The present invention relates to a novel compound possessing excellent herbicidal, germicidal, and acaricidal activities represented by the general formula

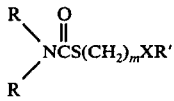

wherein R represents a lower alkyl group; R' represents a group shown by the formula

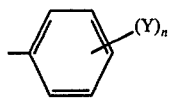

wherein Y represents a halogen atom, an alkyl group, an alkoxy group, a nitro group, a methylthio group, or a trifluoromethyl group and $n$ is an integer of 0 to 3), a benzyl group, a methylbenzyl group, or a naphthyl group; X represents an oxygen atom or a sulfur atom; and $m$ is an integer of 3 to 6.

The invention also relates to a herbicidal, germicidal, and acaricidal composition containing as the active ingredient the compound shown by the above-described general formula. Furthermore, the invention relates to a process of producing the compound of the general formula.

The compound of this invention shown by the abovedescribed general formula is useful as herbicides, germicides, and acaricides.

As herbicides, the compound of this invention shows excellent herbicidal activity to various kinds of weeds by applying it to the water surface of paddy fields or treating soils with the compound. That is, the compound of this invention shows a high herbicidal effect to such weeds as, for example, Slender spikerush (*Eleocharis acicurlaris* var. Roem), *Scirpus juncoides, Cyperus serotinus, Eleocharis kurokuwai, Monochoria vaginalis, Rotola indica Koehne, Dopatrium junceum,* Barnyard grass (*Echinochloa crus-galli*), *Cyperus microiria, (Digitaria adscendens*), Goosegrass (*Eleusine indica*), Green foxtail (*Sataria viridis*), Purple nutsedge (*Cyperus rotundus*), Quack grass (*Agropyron repens*), *Oxalis martiuna, Rumex japonicus, Chenopodium album,* Pig weed (*Amaranthus retroflexus*), *Polygonum nodosum,* Common purslane (*Portulace oleraca*), Annual fleabane (*Erigeron annus*), etc.

When the compound of this invention is used as germicides, the compound is effective for preventing the occurence of rice blast (*piricularia oryzae*) downy mildew, anthracnose, etc., in rice plants, cucumbers, etc.

The compound of this invention is also useful as acaricides. That is, the compound shows an acaricidal activity to plants parasitic mites, such as Citrus red mite (*Panonychus citri Mcgregor*), European red mite (*Panonychus ulmi Koch*), Two spotted spider mite (*Tetranychus urticae Koch*), Carmine mite (*Tetranychus telarius Linne*), Kanazawa spider mite (*Tetranychus kanzawai Kishida*), Sugi spider mite (*Oligonychus bondoensis Ahara*), Clover mite (*Bryobia Praetiosa Koch*), etc., which give damages to plants such as citrus fruits, apples, pears, tea leaves, cotton plants, eggplants, cucumbers, strawberries, roses, carnations, chrysanthemums, Japan cedars, etc., as well as to animal parasitic mites such as *Boophilusmicroplus, Haemaphysalis bispinosa, Amblyomma testadinarium.*

Furthermore, the compound of this invention shows less toxicity to men and beasts as well as fish and shellfishes and thus can be applied safely in wide field.

In U.S. Pat. Nos. 3,166,401; 3,225,078; and 3,284,184, A. G. Weiss et al disclose the compound of the general formula

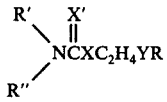

wherein R represents a phenyl group or a halogen-substituted phenyl group; Y represents an oxygen atom or a sulfur atom; X and X' represent an oxygen atom or a sulfur atom at least one of which is a sulfur atom and R and R' represent a lower alkyl group, a cycloalkyl group, an allyl group, a chloroallyl group, a piperidinyl group including a nitrogen atom, etc., and also disclose the production process of the compound and that the compound is useful as herbicides.

The compound of this invention shows, however, higher herbicidal activity to weeds and less phytotoxicity to rice plants or paddies than the compounds disclosed in the aforesaid patents. That is, the compound of this invention is superior to the known compounds in better selectivity between weeds and rice plants. Still further, the compound of this invention has germicidal activity and acaricidal activity as mentioned above.

In particular, since mites pass through their entire life cycles or generations in about 20 days and thus produce about 18 times of generations a year, the number of applying acaricides increases, which imparts to mites resistance or immunity to the acaricides, and thus it is, in fact, a cause of trouble to eliminate the endowment such resistance or immunity. Therefore, it has been strongly demanded to develope acaricides which can be applied to mites in any stages of egg, larval, and adult without endowing them the resistance to the chemicals. The compound of this invention can meet the aforesaid demand and is particularly superior in ovoicidal and adulticidal activities.

The compound of this invention represented by the above-described general formula may be prepared by the following manners.

That is, according to an embodiment of the production processes, the compound of formula I

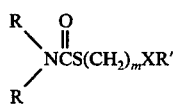  I is prepared by reacting the compound represented by formula II

  II and the compound represented by the formula

Z(CH$_2$)$_m$XR'  III wherein R represents a lower alkyl group; M represents an alkali metal or a quaternarized amine; Z represents a halogen atom; R' represents a group shown by

(wherein Y represnts a halogen atom, an alkyl group, an alkoxy group, a nitro group, a methylthio group, or a trifluoromethyl group and n is an integer of 0 to 3), a benzyl group, a methylbenzyl group, or a naphthyl group; X represents an oxygen atom or a sulfur atom; and m is an integer of 3 to 6, in a solvent such as water, acetone, dimethylformamide, an alcohol, a cellosolve, ether, benzene, toluene, xylene, etc., at temperatures of about 0° to 100° C for 1 to 20 hours.

Furthermore, according to other embodiment of the production processes of this invention, the compound of general formula I is prepared by reacting the compound represented by formula IV

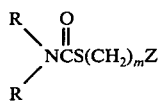

and the compound represented by formula V

HXR'  V wherein R represents a lower alkyl group; Z represents a halogen atom; m represents an integer of 3 to 6; R' represents a group shown by

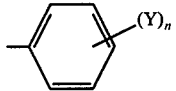

(wherein Y represents a halogen atom, an alkyl group, an alkoxy group, a nitro group, a methylthio group, or a trifluoromethyl group and n is an integer of 0 to 3), a benzyl group, a methylbenzyl group, or a naphtyl group; and X represents an oxygen atom or a sulfur atom, in a solvent such as water, acetone, dimethylformamide, an alcohol, a cellosolve, an ether, benzene, toluene, xylene, etc., at temperatures of from −10° C to 100° C for 1 to 20 hours using a dehydrohalogenating agent such as sodium hydroxide, potassium hydroxide, sodium carbonate, potassium carbonate, sodium bicarbonate, triethylamine, pyridine, etc.

According to still other embodiment of the production processes of this invention, the aimed compound of general formula I is also prepared by reacting the compound represented by formula VI

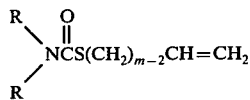

and the compound represented by formula V

HXR'  V wherein R represents a lower alkyl group; m is an integer of 3 to 6; R' represents a group shown by formula

(Y represents a halogen atom, an alkyl group, an alkoxy group, a nitro group, a methylthio group, or a trifluoromethyl group and n is an integer of 0 to 3), a benzyl group, a methylbenzyl group, or a naphthyl group; and X represents an oxygen atom or a sulfur atom, in a non-solvent or a reaction solvent such as benzene, toluene, n-hexane, etc., at temperatures of from room temperature to 150° C for 5 to 20 hours in the absence of catalyst or in the presence of an addition accelerating catalyst such as benzoyl oxide, phosphoric acid, sulfuric acid, etc., or ultraviolet rays.

Then, the process of producing the aimed compound of general formula I will be explained more practically by referring to the following examples.

REFERENCE PRODUCTION EXAMPLE 1

Production of sodium N,N-dimethylthiocarbamate:

In 60 ml of water was dissolved 2.0 g (0.05 mole) of sodium hydroxide and after ice-cooling the solution to 5° C, 5.6 g (0.05 mole) of an aqueous solution of 40% dimethylamine with stirring. Then, 1,4 liter (0.6 mole) of carbonyl sulfide gas was gradually blown into the solution over a period of about 50 minutes. Thereafter, the temperature of the reaction mixture was raised to room temperature and the reaction mixture was stirred for 30 minutes to provide sodium N,N-dimethylthiolcarbamate.

EXAMPLE 1

Production of S-3-(3'-methylphenoxy)propyl-N,N-dimethylthiolcarbamate:

To sodium N,N-dimethylthiolcarbamate prepared in Reference production example 1 was added 50 ml of a dimethylformamide solution having dissolved therein 9.2 g (0.05 mole) of 3-(3'-methylphenoxy)propyl chloride and the mixture was stirred for about 5 hours at 70° to 80° C. After the reaction was over, the reaction mixture was poured in water, the oily material formed was extracted with benzene, and the benzene layer formed was collected, washed with water, and dried by anhydrous sodium sulfate. The benzene solution was concentrated and the residue formed was distilled under a reduced pressure to provide 9.7 g (yield of 76.3%) of a pale-yellow transparent oil having a boiling point of 138° to 139° C/0.02 mmHg and n$_D^{20}$ of 1.5452.

EXAMPLE 2

Production of S-3-(phenoxy)propyl-N,N-dimethylthiolcarbamate:

By following the same procedure as in Example 1 except that 10.8 g (0.05 mole) of 3-phenoxy)propyl bromide was used in place of 3-(3'-methylphenoxy)propyl bromide, 10.1 g (yield of 84.2%) of yellow transparent oil having a boiling point of 130° to 133° C/0.02 mmHg and n$_D^{20}$ of 1.5515 was obtained.

EXAMPLE 3

Production of S-3-(phenoxy)propyl-N,N-dimethylthiolcarbamate:

By following the same procedure as in Reference Production example 1 except that 3.7 g (0.05 mole) of diethylamine was used in place of dimethylamine, sodium N,N-diethylthiol carbamate was produced and by reacting the product thus obtained and 10.8 g (0.05 mole) of 3-phenoxypropyl bromide as in Example 1, 10.9 g (yield of 81.3% of an orange viscous oil having a boiling point of 142° to 144° C/0.02 mmHg and $n_D^{20}$ of 1.5386 was obtained.

EXAMPLE 4

Production of S-3-(phenylthio)propyl-N,N-dimethylthiolcarbamate:

To sodium N,N-dimethylthiolcarbamate prepared in Reference production example 1 was added 50 ml of a dimethylformamide solution having dissolved therein 9.3 g (0.05 mole) of 3-(phenylthio)propyl chloride and the mixture was stirred for about 3 hours at 50° to 60° C. Aftr the reaction was over, the reaction product was poured in water and the oily material formed was extracted with benzene. The benzene layer formed was collected, washed with water, and dried by anhydrous sodium sulfate. The benzene solution was concentrated and the residue thus formed was distilled under a reduced pressure to provide 11.3 g (yield of 88.0%) of a pale-yellow transparent oil having a boiling point of 130° to 132° C/0.06 mmHg and $n_D^{20}$ of 1.5872.

EXAMPLE 5

Production of S-3-(phenylthio)propyl-N,N-dimethylthiolcarbamate:

By following the same procedure as in Reference production example 1 except that 3.7 g (0.05 mole) of diethylamine was used in place of dimethylamine, sodium N,N-diethylthiolcarbamate and then by following the same procedure as in Example 4 using sodium N,N-diethylthiolcarbamate, 11.7 g (yield of 82.4%) of a pale-yellow transparent oil having a boiling point of 133 to 136° C/0.05 mmHg and $n_D^{20}$ of 1.5700 was obtained.

EXAMPLE 6

Production of S-3-(phenylthio)propyl-N,N-di-n-propylthiolcarbamate:

By following the same procedure as in Reference production example 1 except that 5.1 g (0.05 mole) of di-n-propylamine was used in place of dimethylamine, sodium N,N-di-n-propylthiolcarbamate was produced and then following the same procedure as in Example 4 using the carbamate thus produced, 13.3 g (yield of 85.3%) of a pale-yellow transparent oil having a boiling point of 148° to 151° C/0.01 mmHg and $n_D^{20}$ of 1.5472 was obtained.

EXAMPLE 7

Production of S-3-(phenylthio)propyl-N,N-di-isopropylthiolcarbamate:

By following the same procedure as in Reference production example 1 except that 5.1 g (0.05 mole) of di-isopropylamine was used in place of dimethylamine and then by following the same procedure as in Example 4 using the carbamate thus produced, 12.2 g (yield of 78.2%) of a pale-yellow transparent oil having a boiling point of 132° to 135° C/0.005 mmHg and $n_D^{20}$ of 1.5602 was obtained.

REFERENCE PRODUCTION EXAMPLE 2

Production of S-3-chloropropyl-N,N-dimethylthiolcarbamate:

In 60 ml of water was dissolved 2.0 g (0.05 mole) of sodium hydroxide and after ice-cooling the solution, 5.6 g (0.05 mole) of an aqueous solution of 40% dimethylamine was addd to the solution with stirring and then 1.4 liters (0.06 mole) of carbonyl sulfide gas was gradually blown into the solution over a period of about 50 minutes. Thereafter, the temperature of the reaction product was raised to room temperature and the reaction product was stirred for 30 minutes.

Then, 20 ml of an acetone solution having dissolved therein 9.4 g (0.06 mole) of 1-bromo-3-chloropropane was added to the reaction product and the mixture was refluxed with stirring for 7 hours. The reaction mixture obtained was allowed to cool and the oily layer formed was extracted with 100 ml of benzene. The benzene layer formed was collected, washed with water, dried by a powder, and then filtered. The filtrate was concentrated and the residue formed was distilled under a reduced pressure to provide 7.7 g (yield of 85.0%) of a colorless transparent oil having a boiling point of 77° to 80° C/0.3 mmHg and $n_D^{20}$ of 1.5116.

EXAMPLE 8

Production of S-3-(phenylthio)propyl-N,N-dimethylthiolcarbamate:

In 100 ml of ethanol was dissolved 2.2 g (0.04 mole) of potassium hydroxide and then 4.4 g (0.04 mole) of thiophenol was added to the solution. Then, 7.3 g (0.04 mole) of S-3-chloropropyl-N,N-dimethylthiolcarbamate produced in Reference production example 2 was added dropwise gradually to the mixture with stirring at room temperature and thereafter, the mixture was refluxed with stirring for about 3 hours. After allowing to cool the reaction mixture, potassium chloride thus precipitated was filtered off and the ethanol solution obtained as the filtrate was concentrated. The residue formed was extracted using 150 ml of benzene and the benzene extract was washed with water and dried by anhydrous sodium sulfate. Then, the benzene solution was concentrated and the residue formed was distilled under a reduced pressure to provide 9.3 g (yield of 91.2%) of a pale-yellow transparent oil having a boiling point of 130° to 132° C/0.006 mmHg and $n_D^{20}$ of 1.5872.

EXAMPLE 9

Production of S-3-(phenylthio)propyl-N,N-diethylthiolcarbamate:

By following the same procedure as in Example 8 except that 8.4 g (0.04 mole) of S-3-chloropropyl-N,N-diethylthiolcarbamate was used in place of S-3-chloropropyl-N,N-diethylthiolcarbamate, 10.3 g (yield of 90.8%) of a pale-yellow transparent oil having a boiling point of 133° to 136° C/0.005 mmHg and $n_D^{20}$ of 1.5700 was obtained.

EXAMPLE 10

Production of S-3-(4'-chlorophenoxy)propyl-N,N-dimethylthiolcarbamate:

In 5 ml of water was dissolved 2.0 g (0.05 mole) of sodium hydroxide and then 40 ml of a dimethylformamide solution having dissolved therein 6.5 g (0.05 mole) of 4-chlorophenol was added to the solution followed by stirring for 30 minutes at room temperature.

Then, to the mixture prepared above was added 20 ml of a dimethylformamide solution having dissolved therein 9.1 g (0.05 mole) of S-3-chloropropyl-N,N-dimethylthiolcarbamate produced in Reference production example 2 and the resultant mixture was stirred for about 5 hours at 70 to 80° C to cause the reaction. After allowing to cool the reaction mixture, it was poured in water and the oily product formed was extracted with benzene. The benzene extract was washed with water and dried by anhydrous sodium sulfate. The benzene solution was concentrated and the residue formed was distilled under a reduced pressure to provide 10.5 g (yield of 79.6%) of a pale-yellow transparent oil having a boiling point of 148° to 150° C/0.02 mmHg (crystallization melting point of 48.5° to 51° C).

EXAMPLE 11

Production of S-3-(2',4'-dichlorophenoxy)propyl-N,N-dimethylthiolcarbamate:

By following the same procedure as in Example 10 except that 8.2 g (0.05 mole) of 2,4-dichlorophenol was used in place of 4-chlorophenol, 9.7 g (yield of 63.0%) of a pale-yellow transparent oil having a boiling point of 166° to 170° C/0.015 mmHg and $n_D^{20}$ of 1.5663 was obtained.

EXAMPLE 12

Production of S-3-(4'-methylphenoxy)propyl-N,N-dimethylthiolcarbamate:

In 100 ml of ethanol was dissolved 2.8 g (0.05 mole) of potassium hydroxide and after adding to the solution 5.4 g (0.05 mole) of 4-methylphenol, the mixture was stirred for 30 minutes at room temperature. Thereafter, 9.1 g (0.05 mole) of S-3-chloropropyl-N,N-dimethylthiolcarbamate was added to the mixture and the resultant mixture was stirred for 5 hours under refluxing to cause the reaction. After the reaction was over, potassium chloride precipitated was filtered off and the ethanol solution formed was concentrated. The residue was extracted with benzene and the benzene extract was washed with water, dried by anhydrous sodium sulfate, and concentrated. Then, by distilling the residue thus formed under a reduced pressure, 9.0 g (yield of 69.8%) of a pale-yellow transparent oil having a boiling point of 141° to 142° C/0.02 mmHg and $n_D^{20}$ of 1.5458 was obtained.

REFERENCE PRODUCTION EXAMPLE 3

Production of S-allyl-N,N-dimethylthiolcarbamate:

In 60 m of water was dissolved 2.0 g (0.05 mole) of sodium hydroxide and after ice-cooling the solution to 5° C, 5.6 g (0.05 mole) of an aqueous solution of 40% dimethylamine was added to the solution with stirring. Then, 1.4 liters (0.06 mole) of carbonyl sulfide gas was gradually blown into the solution over a period of about 50 minutes and thereafter, the temperature of the reaction mixture was raised to room temperature followed by stirring for 30 minutes.

Thereafter, 20 ml of an acetone solution having dissolved therein 7.3 g (0.06 mole) of allyl bromide was added to the reaction mixture and the resultant mixture was refluxed for 7 hours with stirring. After allowing to cool, the oily layer formed was extracted with 100 ml of benzene and the benzene extract was washed with water and dried by a powder of sodium sulfate followed by filtration. The filtrate was concentrated and the residue formed was distilled under a reduced pressure to provide 6.0 g (yield of 82.0%) of a colorless transparent oil having a boiling point of 110° to 112° C/22 mmHg and $n_D^{20}$ of 1.5075.

EXAMPLE 13

Production of S-3-(phenylthio)propyl-N,N-dimethylthiolcarbamate:

A mixture of 7.3 g (0.05 mole) of S-allyl-N,N-dimethylthiolcarbamate prepared in Reference production example 3 and 5.5 g (0.05 mole) of thiophenol was stirred for about 15 hours at 100° to 110° C. After the reaction was over, 150 ml of benzene was added to the reaction mixture and after washing with an aqueous 3% sodium hydroxide solution and then water, the reaction mixture was dried with anhydrous sodium sulfate. The benzene solution obtained was concentrated and the residue formed was distilled under a reduced pressure to provide 4.8 g (yield of 35%) of a pale-yellow transparent oil having a boiling point of 130° to 132° C/0.006 mmHg and $n_D^{20}$ of 1.5872.

Typical examples of the compounds of this invention prepared by the process of this invention including the abovedescribed examples are illustrated below.

Compound 1: S-3-(phenoxy)propyl-N,N-dimethylthiolcarbamate, a pale-yellow transparent oil boiling at 130° to 133° C/0.02 mmHg, $n_D^{20}$ 1.5515.

Compound 2: S-3-(phenoxy)propyl-N,N-diethylthiolcarbamate, an orange viscous oil boiling at 142° to 144° C/0.02 mmHg, $n_D^{20}$ 1.5386.

Compound 3: S-3-(phenoxy)propyl-N,N-di-n-propylthiolcarbamate, an orange viscous oil boiling at 152° to 154° C/0.02 mmHg, $n_D^{20}$ 1.5290.

Compound 4: S-3-(phenoxy)propyl-N,N-di-isopropylthiolcarbamate, an orange viscous oil boiling at 144° to 146° C/0.02 mmHg, $n_D^{20}$ 1.5290.

Compound 5: S-3-(4'-chlorophenoxy)propyl-N,N-dimethylthiolcarbamate, a pale-yellow transparent oil (crystallizable) melting at 48.5° to 51° C.

Compound 6: S-3-(2'-chlorophenoxy)propyl-N,N-dimethylthiolcarbamate, a colorless transparent oil boiling at 140° to 145° C/0.015 mmHg, $n_D^{20}$ 1.5621.

Compound 7: S-3-(4'-bromophenoxy)propyl-N,N-dimethylthiolcarbamate, a pale-red transparent oil boiling at 153° to 155° C/0.01 mmHg, $n_D^{20}$ 1.5741.

Compound 8: S-3-(4'-methylphenoxy)propyl-N,N-dimethylthiolcarbamate, a pale-yellow transparent oil boiling at 141° to 142° C/0.02 mmHg, $n_D^{20}$ 1.5458.

Compound 9: S-3-(3'-methylphenoxy)propyl-N,N-dimethylthiolcarbamate, a pale-yellow transparent oil boiling at 138° to 139° C/0.02 mmHg, $n_D^{20}$ 1.5452.

Compound 10: S-3-(2'-methylphenoxy)propyl-N,N-dimethylthiolcarbamate, a colorless transparent oil boiling at 135° to 137° C/0.01 mmHg, $n_D^{20}$ 1.5485.

Compound 11: S-3-(4'-tert-butylphenoxy)propyl-N,N-dimethylthiolcarbamate, a pale-red transparent oil boiling at 155° to 157° C/0.005 mmHg, $n_D^{20}$ 1.5332.

Compound 12: S-3-(2',4'-dichlorophenoxy)propyl-N,N-dimethylthiolcarbamate, a pale-yellow transparent oil boiling at 166° to 170° C/0.015 mmHg, $n_D^{20}$ 1.5663.

Compound 13: S-3-(4'-nitrophenoxy)propyl-N,N-dimethylthiolcarbamate, a pale-yellow fine needle crystal melting at 99° to 100° C.

Compound 14: S-3-(4'-methylthiphenoxy)propyl-N,N-dimethylthiolcarbamate, a pale-yellow transparent oil boiling at 162° to 165° C/0.015 mmHg.

Compound 15: S-3-(1-naphthoxy)propyl-N,N-dimethylthiolcarbamate, a yellow transparent oil boiling at 182° to 188° C/0.02 mmHg, $n_D^{20}$ 1.6018.

Compound 16: S-3-(2-naphthoxy)propyl-N,N-dimethylthiolcarbamate, a pale-brown crystal metling at 86° to 88° C.

Compound 17: S-3-(3'-methylbenzyloxy)propyl-N,N-dimethylthiolcarbamate, a yellow oil boiling at 154° C/0.01 mmHg, $n_D^{20}$ 1.5539.

Compound 18: S-4-phenoxybutyl-N,N-dimethylthiolcarbamiate, a colorless oil boiling at 155° C/0.02 mmHg, $n_D^{20}$ 1.5473.

Compound 19: S-5-(phenoxy)pentyl-N,N-dimethylthiolcarbamate, a colorless transparent oil boiling at 141° to 145°C/0.005 mmHg, $n_D^{20}$ 1.5368.

Compound 20: S-6-(phenoxy)hexyl-N,N-dimethylthiolcarbamate, a white prismatic crystal metling at 58° to 59° C.

Compound 21: S-4-(3'-chlorophenoxy)butyl-N,N-dimethylthiolcarbamate, a colorless transparent oil boiling at 142° to 149°C/0.008 mmHg, $n_D^{20}$ 1.5560.

Compound 22: S-4-(2',4'-dichlorophenoxy)butyl-N,N-dimethylthiolcarbamate, a white crystal melting at 43° to 47° C.

Compound 23: S-4-(2',4',6'-trichlorophenoxy)butyl-N,N-dimethylthiolcarbamat, a colorless transparent oil boiling at 175° to 180° C/0.013 mmHg, $n_D^{20}$ 1.5670.

Compound 24: S-4-(3'-methyl-4'-chlorophenoxy)butyl-N,N-dimethylthiolcarbamate, a colorless prismatic crystal metling at 55° to 56° C.

Compound 25: S-4-(3'-methylphenoxy)butyl-N,N-dimethylthiolcarbamate, a colorless oil boiling at 135°C/0.1 mmHg, $n_D^{20}$ 1.5450.

Compound 26: S-6-(3'-methylphenoxy)hexyl-N,N-dimethylthiolcarbamate, a colorless transparent oil boiling at 165° to 166°C/0.005 mmHg, $n_D^{20}$ 1.5368.

Compound 27: S-4-(3'-methyl-4'-iso-propylphenoxy)butyl-N,N-dimethylthiolcarbamate, a colorless transparent oil boiling at 175° to 181°C/0.015 mmHg, $n_D^{20}$ 1.5339.

Compound 28: S-4-(3'-trifluoromethylphenoxy)butyl-N,N-dimethylthiolcarbamate, a yellow transparent oil boiling at 130° to 135°C/0.01 mmHg, $n_D^{20}$ 1.5038.

Compound 29: S-3-(phenylthio)propyl-N,N-dimethylthiolcarbamate, a pale-yellow transparent oil boiling at 130°to 132°C/0.006 mmHg, $n_D^{20}$ 1.5872.

Compound 30: S-3-(4'-methylphenylthio)propyl-N,N-dimethylthiolcarbamate, a pale-yellow transparent oil boiling at 147° to 150°C/0.008 mmHg, $n_D^{20}$ 1.5805.

Compound 31: S-3-(2'-isopropylphenylthio)propyl-N,N-dimethylthiolcarbamate, a pale-yellow transparent oil boiling at 151° to 154°C/0.007 mmHg, $n_D^{20}$ 1.5715.

Compound 32: S-3-(4'-chlorophenylthio)propyl-N,N-dimethylthiolcarbamate, a pale-yellow transparent oil boiling at 160° to 163°C/0.007 mmHg, $n_D^{20}$ 1.5936.

Compound 33: S-3-(phenylthio)propyl-N,N-diethylthiolcarbamate, a pale-yellow transparent oil boiling at 133° to 136°C/0.005 mmHg, $n_D^{20}$ 1.5700.

Compound 34: S-3-(phenylthio)propyl-N,N-di-n-propylthiolcarbamate, a pale-yellow transparent oil boiling at 148° to 151°C/0.01 mmHg, $n_D^{20}$ 1.5472.

Compound 35: S-3-(phenylthio)propyl-N,N-di-iso-propylthiolcarbamate, a pale-yellow transparent oil boiling at 132° to 135°C/0.005 mmHg, $n_D^{20}$ 1.5602.

Compound 36: S-4-(phenylthio)butyl-N,N-dimethylthiolcarbamate, a yellow transparent oil boiling at 151° to 152°C/0.02 mmHg, $n_D^{20}$ 1.5761.

Compound 37: S-5-(phenylthio)pentyl-N,N-dimethylthiolcarbamate, a colorless transparent oil boiling at 162° to 163°C/0.01 mmHg, $n_D^{20}$ 1.5731.

Compound 38: S-6-(phenylthio)hexyl-N,N-dimethylthiolcarbamate, a colorless transparent oil boiling at 163° to 165°C/0.05 mmHg, $n_D^{20}$ 1.5652.

Compound 39: S-4-(4'-thiomethylphenylthio)butyl-N,N-dimethylthiolcarbamate, a yellow viscous oil boiling at 193° to 194°C/0.008 mmHg, $n_D^{20}$ 1.6145.

Compound 40: S-4-(4'-nitrophenylthio)butyl-N,N-dimethylthiolcarbamate, a yellow fine needle crystal melting at 68° to 69° C.

Compound 41: S-3-(benzylthio)propyl-N,N-dimethyl-thiolcarbamate, a pale-yellow transparent oil boiling at 139.5°C/0.01 mmHg, $n_D^{20}$ 1.5735.

Compound 42: S-4-(3'-methoxyphenoxy)butyl-N,N-dimethylthiolcarbamate, a yellow transparent oil boiling at 160° to 165°C/0.01 mmHg, $n_D^{20}$ 1.5490.

In the case of using these compounds as herbicides, germicides, or acaricides, dusts, fine powders, granules, fine granules, emulsions, solution, wettable powders, etc., of these compounds are prepared from these compounds alone or, preferably, from these compounds and adjuvants such as extenders, solvents, wetting agents, emulsifying agents, sticking agents, dispersing agents, etc., for example, talc, kaolin, clay, diatomaceous earth, silicon dioxide, vermiculite, chalk, alcohols, ketones, cyclohexane, dimethylformamide, DMSO, toluene, xylene, petroleum solvents, polyoxyethylene alkylaryl ether, polyoxyethylene sorbitan monolaurate, alkylaryl sulfonic acid salts lignin sulfonic acid salts, polyvinyl alcohol, methyl cellulose, etc.

The herbicidal, germicidal, or acaricidal formulations or compositions thus prepared are applied to weeds, fungi, or mites as follows:

That is, when the formulation are solution, the solution containing 1 to 2,000 ppm of the active ingredient is applied at an amount of 10 to 500 liters per 10 acres.

When the formulations are dust, the dust containing 0.1 to 10% active ingredient is applied at an amount of 0.5 to 5 kg per 10 acres.

Furthermore, when the formulation are granule, the granules are applied on the surface of soil or in soil at an amount same as in case of applying the dust.

Then, the formulatiomn containing the compounds of this invention will be explained practically together with biological activity tests of them.

FORMULATION EXAMPLE 1

Emulsion;

An emulsion of Compound 1 was prepared by uniformly mixing 50 parts by weight of Compound 1, 35 parts by weight of xylene, 12 parts by weight of polyoxyethylene alkylaryl ether, and 3 parts by weight of calcium alkylbenzenesulfonate.

At use, the emulsion was diluted with water, etc., and applied as a spray.

FORMULATION EXAMPLE 2

Wettable powder:

A wettable powder of Compound 2 was prepared by uniformly mixing 20 parts by weight of Compound 2, 35 parts of diatomaceous earth, 5 parts of silicon dioxide, and 5 parts of sodium ligninsulfonate followed by grinding.

At use, the wettable powder was diluted with water, etc., and applied as a spray.

FORMULATION EXAMPLE 3

Dust:

A dust containing Compound 3 was prepared by uniformly mixing 3 parts by weight of Compound 3, 47 parts of talc, 47 parts of clay, and 3 parts of silicon dioxide.

At use, the dust was directly applied.

FORMULATION EXAMPLE 4

Granule:

A granule containing Compound 4 was prepared by uniformly mixing 5 parts by weight of Compound 4, 15 parts of bentonite, 47.5 parts of talc, 30 parts of clay, 2 parts of sodium ligninsulfonate, and 0.5 part of sodium dodecylbenzenesulfonate followed by grinding, mixing the ground mixture with 25 parts of water, granulating the mixture by means of an extrusion type granulator, drying, and sieving the granules thus formed.

At use, the granule was directly applied.

EXPERIMENT 1

Test on transplanted rice plant and paddy field weeds:

A soil uniformly containing the subterranean stems of Slender spikerush (*Eleocharis acicularis*) and *Scirpus juncoides* was filled in poreclain pots each having a diamter of 30 cm and the seeds of barnyard grass and *Monochoria vaginalis* were sowed at 50 grains per pot. Then, rice plants (rice species: Kinmaze) of two leaves period were transplanted at 5 plants per pot and then water was filled in each spot at a depth of 3 cm. Thereafter, when the barnyard grass emerged to one leaf period, a predetermined amount of an emulsion prepared according to the procedure as in Formulation 1 shown above was uniformly allied onto the water surface. After 14 days since the application of the emulsion, the weed inhibition rate and the phytotoxicity were measured. The result is shown in Table 1.

Table 1

| Test Comp. No. | Active Ingredient (g/10a) | Weed inhibition rate | | | | Phytotoxicity to rice plant |
| --- | --- | --- | --- | --- | --- | --- |
| | | Slender spikerush | Scirpus juncoides | Barnyard grass | Monochoria vaginalis | |
| Compound (1) | 500 | 5 | 5 | 5 | 5 | none |
| | 250 | 5 | 5 | 5 | 5 | " |
| Compound (2) | 500 | 5 | 5 | 5 | 5 | " |
| | 250 | 5 | 5 | 5 | 5 | " |
| Compound (3) | 500 | 5 | 5 | 5 | 5 | " |
| | 250 | 5 | 5 | 5 | 5 | " |
| Compound (4) | 500 | 5 | 5 | 5 | 5 | " |
| | 250 | 5 | 5 | 5 | 5 | " |
| Compound (5) | 500 | 5 | 5 | 5 | 5 | " |
| | 250 | 5 | 5 | 5 | 5 | " |
| Compound (6) | 500 | 5 | 5 | 5 | 5 | " |
| | 250 | 5 | 5 | 5 | 5 | " |
| Compound (7) | 500 | 5 | 5 | 5 | 5 | " |
| | 250 | 5 | 5 | 5 | 5 | " |
| Compound (8) | 500 | 5 | 5 | 5 | 5 | " |
| | 250 | 5 | 5 | 5 | 5 | " |
| Compound (9) | 500 | 5 | 5 | 5 | 5 | " |
| | 250 | 5 | 5 | 5 | 5 | " |
| Compound (10) | 500 | 5 | 5 | 5 | 5 | " |
| | 250 | 5 | 5 | 5 | 5 | " |
| Compound (11) | 500 | 5 | 5 | 5 | 5 | " |
| | 250 | 5 | 5 | 5 | 5 | " |
| Compound (12) | 500 | 5 | 5 | 5 | 5 | " |
| | 250 | 5 | 5 | 5 | 5 | " |
| Compound (13) | 500 | 5 | 5 | 5 | 5 | " |
| | 250 | 5 | 5 | 5 | 5 | " |
| Compound (14) | 500 | 5 | 5 | 5 | 5 | " |
| | 250 | 5 | 5 | 5 | 5 | " |
| Compound (15) | 500 | 5 | 5 | 5 | 5 | " |
| | 250 | 5 | 5 | 5 | 5 | " |
| Compound (16) | 500 | 5 | 5 | 5 | 5 | " |
| | 250 | 5 | 5 | 5 | 5 | " |
| Compound (17) | 500 | 5 | 5 | 5 | 5 | " |
| | 250 | 5 | 5 | 5 | 5 | " |
| Compound (18) | 500 | 5 | 5 | 5 | 5 | " |
| | 250 | 5 | 5 | 5 | 5 | " |
| Compound (21) | 500 | 5 | 5 | 5 | 5 | " |
| | 250 | 5 | 5 | 5 | 5 | " |
| Compound (22) | 500 | 5 | 5 | 5 | 5 | " |
| | 250 | 5 | 5 | 5 | 5 | " |
| Compound (24) | 500 | 5 | 5 | 5 | 5 | " |
| | 250 | 5 | 5 | 5 | 5 | " |
| Compound (28) | 500 | 5 | 5 | 5 | 5 | " |
| | 250 | 5 | 5 | 5 | 5 | " |
| Compound (29) | 500 | 5 | 5 | 5 | 5 | " |
| | 250 | 5 | 5 | 5 | 5 | " |
| Compound (30) | 500 | 5 | 5 | 5 | 5 | " |
| | 250 | 5 | 5 | 5 | 5 | " |
| Compound (31) | 500 | 5 | 5 | 5 | 5 | " |
| | 250 | 5 | 5 | 5 | 5 | " |
| Compound (32) | 500 | 5 | 5 | 5 | 5 | " |
| | 250 | 5 | 5 | 5 | 5 | " |
| Compound (33) | 500 | 5 | 5 | 5 | 5 | " |
| | 250 | 5 | 5 | 5 | 5 | " |
| Compound (34) | 500 | 5 | 5 | 5 | 5 | " |
| | 250 | 5 | 5 | 5 | 5 | " |
| Compound (35) | 500 | 5 | 5 | 5 | 5 | " |
| | 250 | 5 | 5 | 5 | 5 | " |
| Compound (36) | 500 | 5 | 5 | 5 | 5 | " |
| | 250 | 5 | 5 | 5 | 5 | " |
| Compound (37) | 500 | 5 | 5 | 5 | 5 | " |
| | 250 | 5 | 5 | 5 | 5 | " |

Table 1-continued

| Test Comp. No. | Active Ingredient (g/10a) | Weed inhibition rate | | | | Phytotoxicity to rice plant |
|---|---|---|---|---|---|---|
| | | Slender spikerush | Scirpus juncoides | Barnyard grass | Monochoria vaginalis | |
| Compound (38) | 500 | 5 | 5 | 5 | 5 | " |
| | 250 | 5 | 5 | 5 | 5 | " |
| Compound (39) | 500 | 5 | 5 | 5 | 5 | " |
| | 250 | 5 | 5 | 5 | 5 | " |
| Compound (40) | 500 | 5 | 5 | 5 | 5 | " |
| | 250 | 5 | 5 | 5 | 5 | " |
| No active ingredient | — | 0 | 0 | 0 | 0 | " |
| Not treated | — | 0 | 0 | 0 | 0 | " |

EXPERIMENT 2

Test for rice blast preventing effect:

A biscuit pot of 9 cm diameter having planted therein 20 rice plant seedling (rice species: Aichiasahi) was placed on a turn table and the wettable powder prepared as in Formulation 2 shown above was diluted with water and applied by means of a spray gun at a spraying pressure of 0.5 kg/cm$^2$ and at an amount of 30 ml per pot. After 3 days since the application of the wettable powder solution, a spore suspension containing 20 rice blast spores in one view of microscope (15 × 10), said rice blast spores having been obtained by continuously innoculating rice plants in green house was inoculated as a spray at a rate of 5 ml per pot.

Thereafter, the pot was placed in an inocluating chamber for 24 hours at saturated humidity and at 24° C and then placed in a green house to keep the pot at a high temperature and to grow the lesios of the rice blast spots. After 7 days since the inoculation of the spore suspension, the number of the lesions was checked about 10 leaves per pot and the preventive value was calculated from the result, the result being shown in Table 2.

$$\text{Disease control (\%)} = \frac{(A) - (B)}{(A)} \times 100$$

wherein (A) is the number of rice blast lesions on non-treated rice plants and (B) is the number of rice blast lesions on treated rice plants.

Table 2

| Test Comp. No. | Concentration (ppm) | Disease control (%) | Phytotoxicity |
|---|---|---|---|
| Comp. (2) | 500 | 100 | none |
| Comp. (3) | 500 | 100 | " |
| Comp. (4) | 500 | 100 | " |
| Comp. (5) | 500 | 100 | " |
| Comp. (6) | 500 | 100 | " |
| Comp. (7) | 500 | 97.9 | " |
| Comp. (8) | 500 | 100 | " |
| Comp. (9) | 500 | 98.4 | " |
| Comp. (10) | 500 | 100 | " |
| Comp. (11) | 500 | 100 | " |
| Comp. (12) | 500 | 100 | " |
| Comp. (14) | 500 | 94.1 | " |
| Comp. (15) | 500 | 91.2 | " |
| Comp. (17) | 500 | 100 | " |
| Comp. (18) | 500 | 100 | " |
| Comp. (19) | 500 | 100 | " |
| Comp. (20) | 500 | 100 | " |
| Comp. (21) | 500 | 100 | " |
| Comp. (22) | 500 | 100 | " |
| Comp. (25) | 500 | 100 | " |
| Comp. (26) | 500 | 98.4 | " |
| Comp. (28) | 500 | 100 | " |
| Comp. (29) | 500 | 100 | " |
| Comp. (30) | 500 | 100 | " |
| Comp. (31) | 500 | 100 | " |
| Comp. (32) | 500 | 100 | " |
| Comp. (33) | 500 | 99.4 | " |
| Comp. (36) | 500 | 100 | " |
| Comp. (37) | 500 | 100 | " |
| Comp. (38) | 500 | 100 | " |
| Comp. (39) | 500 | 100 | " |
| Comp. (40) | 500 | 100 | " |
| Comp. (42) | 500 | 100 | " |
| No active ingredient | — | 0 | " |
| Not treated | — | 0 | " |

EXPERIMENT 3

Test of ovocidal effect on Citrus red mite (panonychus citri):

The female adults of Citrus red mite were inoculated to a summer orange (Chinese citron) of two year age cultivated in a biscuit pot of 15 cm diameter in a green house at 50 mites per pot to lay 50 to 100 eggs. Thereafter, the adults were removed and the emulsion prepared as in Formulation 1 shown above was diluted to a definite concentration and applied as a spray at 30 ml per pot. After 10 days since the application of the emulsion, the mortality rate was checked, the result being shown in Table 3.

Table 3

| Test Comp. No. | Mortality Rate (%) | | Phytotoxicity |
|---|---|---|---|
| | 100 ppm | 50 ppm | |
| Comp. (1) | 100 | 100 | none |
| Comp. (2) | 100 | 93.9 | " |
| Comp. (3) | 100 | 84.3 | " |
| Comp. (4) | 100 | 63.4 | " |
| Comp. (5) | 100 | 93.9 | " |
| Comp. (6) | 100 | 100 | " |
| Comp. (7) | 80.5 | 51.1 | " |
| Comp. (9) | 100 | 100 | " |
| Comp. (10) | 100 | 100 | " |
| Comp. (11) | 100 | 100 | " |
| Comp. (12) | 97.8 | 77.7 | " |
| Comp. (14) | 100 | 97.7 | " |
| Comp. (17) | 100 | 100 | " |
| Comp. (18) | 100 | 100 | " |
| Comp. (19) | 100 | 100 | " |
| Comp. (20) | 100 | 100 | " |
| Comp. (21) | 100 | 100 | " |
| Comp. (22) | 100 | 77.6 | " |
| Comp. (23) | 100 | 100 | " |
| Comp. (24) | 100 | 80.7 | " |
| Comp. (25) | 100 | 100 | " |
| Comp. (26) | 100 | 75.5 | " |
| Comp. (27) | 100 | 91.4 | " |
| Comp. (28) | 100 | 100 | " |
| Comp. (29) | 100 | 100 | " |
| Comp. (30) | 100 | 100 | " |
| Comp. (31) | 100 | 100 | none |
| Comp. (32) | 100 | 100 | " |
| Comp. (33) | 100 | 100 | " |
| Comp. (34) | 100 | 100 | " |
| Comp. (35) | 100 | 100 | " |
| Comp. (36) | 100 | 100 | " |
| Comp. (37) | 100 | 100 | " |
| Comp. (38) | 100 | 100 | " |
| Comp. (39) | 100 | 100 | " |
| Comp. (40) | 100 | 100 | " |
| Comp. (41) | 100 | 100 | " |
| Comp. (42) | 100 | 100 | " |
| No active | 0 | 0 | " |

Table 3-continued

| Test Comp. No. | Mortality Rate (%) | | Phytotoxicity |
|---|---|---|---|
| | 100 ppm | 50 ppm | |
| Not treated | 0 | 0 | " |

EXPERIMENT 4

Test on Citrus red mite having resistance to organic phosphorus compounds:

The adulsts of Citrus red mite having resistance more than about 10 times to organic phosphorus compounds were applied to summer orange(Chinese citron) seedlings cultivated in a pot of 15 cm diameter in a green house at 100 mites per pot an after 10 days since the application, the emulsion prepared as in Formulation 1 shown above was diluted to a concentration of 500 ppm and applied as a spray at 30 ml per pot. Thereafter, the number of the living mites were conted with the passage of time, the result being shown in Table 4.

Table 4

| Test Comp. No. | No. of mites after application | | | | | |
|---|---|---|---|---|---|---|
| | (I) | (II) | (III) | (IV) | (V) | (VI) |
| Compound 1 | 112 | 0 | 0 | 0 | 0 | 0 |
| Compound 9 | 95 | 0 | 0 | 0 | 0 | 1 |
| Compound 18 | 105 | 0 | 0 | 0 | 0 | 0 |
| Compound 25 | 121 | 0 | 0 | 0 | 1 | 4 |
| Control 1* | 98 | 91 | 136 | 147 | 241 | 183 |
| Control 2* | 97 | 115 | 155 | 229 | 236 | 216 |

(I): Number of mites before application.
(II): After 4 days since the application,
(III): after 8 days,
(IV) after 16 days,
(V): after 32 days, and
(VI): after 64 days.
Control 1* An emulsion containing no active ingredient of this invention was applied.
Control 2* Not treated.

While the invention has been described in detail and with reference to specific embodiments thereof, it will be apparent to on skilled in the art that various changes and modifications can be made therein without departing from the spirit and scpe thereof.

What is claimed is:

1. A thiolcarbamate derivative having the following general formula

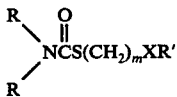

wherein R represents a lower alkyl group; R' represents a group shown by

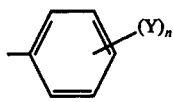

wherein Y represents a halogen atom, an alkyl group having 1-4 carbon atoms, an alkoxy group having 1-4 carbon atoms, a nitro group, a methylthio group or trifluoromethyl group and n is an integer of 0 to 3, a benzyl group, a methylbenzyl group or naphthyl group; X represents an oxygen atom or sulfur atom; and m is an integer of 3 to 6.

2. A thiolcarbamate derivative according to claim 1 represented by the following general formula

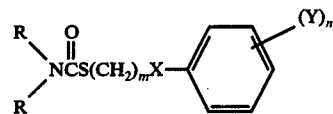

wherein R represents said lower alkyl group; Y represents a halogen atom, said alkyl group, said alkoxy group of methylthio group; X represents an oxygen atom or sulfur atom; m is an integer of 3 to 6; and n is an integer of 0 to 3.

3. A thiolcarbamate derivative as claimed in claim 1 which is S-3-(phenoxy)propyl-N,N-dimethylthiolcarbamate.

4. A thiolcarbamate derivative as claimed in claim 1 which is S-3-(3'-methylphenoxy)propyl-N,N-dimethylthiolcarbamate.

5. A thiolcarbamate derivative as claimed in claim 1 which is S-4-(phenoxy)butyl-N,N-dimethylthiolcarbamate.

6. A germicidal, and acaricidal composition containing as the active ingredient a compound represented by the general formula

wherein R represents a lower alkyl group; R' represents a group shown by

wherein Y represents a halogen atom, an alkyl group having 1-4 carbon atoms, an alkoxy group having 1-4 carbon atoms, a nitro group, a methylthio group, or a trifluoromethyl group, and n is an integer of 0 to 3, a benzyl group, a methylbenzyl group, or a naphthyl group; X represents an oxygen atom or a sulfur atom; and m is an integer of 3 to 6.

7. A method for controlling fungi, or mites which comprises applying germicidally or acaricidally effective amount of the thiolcarbamate derivative having the general formula

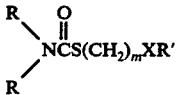

wherein R represents a lower alkyl group; R' represents a group shown by the formula

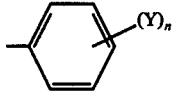

wherein Y represents a halogen atom, an alkyl group having 1-4 carbon atoms, an alkoxy group having 1-4 carbon atoms, a nitro group, a methylthio group, or a trifluoromethyl group, and n is an integer of 0 to 3, a benzyl group, a methylbenzyl group, or a naphthyl group; X represents an oxygen atom or a sulfur atom; and m is an integer of 3 to 6.

8. The thiolcarbamate derivative of claim 1 wherein said alkoxy group having 1-4 carbon atoms is a methoxy group.

9. The composition of claim 6 wherein said alkoxy group having 1-4 carbon atoms is a methoxy group.

10. The method of claim 7 wherein said alkoxy group having 1-4 carbon atoms is a methoxy group.

* * * * *